United States Patent
Khalifa et al.

(10) Patent No.: US 10,239,875 B2
(45) Date of Patent: *Mar. 26, 2019

(54) NAPHTHYRIDINYL HYDRAZINE DERIVATIVES AS POTENT PERIPHERAL ANALGESIC AGENTS

(71) Applicant: KING SAUD UNIVERSITY, Riyadh (SA)

(72) Inventors: Nagy Mahmoud Hassan Khalifa, Riyadh (SA); Mohamed A. Al-Omar, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/624,811

(22) Filed: Jun. 16, 2017

(65) Prior Publication Data
US 2018/0362524 A1 Dec. 20, 2018

(51) Int. Cl.
*C07D 471/04* (2006.01)

(52) U.S. Cl.
CPC ............... *C07D 471/04* (2013.01)

(58) Field of Classification Search
CPC .................................. C07D 471/04
See application file for complete search history.

(56) References Cited

U.S. PATENT DOCUMENTS

| | | | |
|---|---|---|---|
| 4,801,592 A | 1/1989 | Graf et al. | |
| 5,780,482 A | 7/1998 | Armitage et al. | |
| 7,432,275 B2 | 10/2008 | Bakthavatchalam et al. | |
| 2007/0232627 A1 | 10/2007 | Betebenner et al. | |
| 2010/0256139 A1 | 10/2010 | Rockway et al. | |

OTHER PUBLICATIONS

Eweas "Synthesis, molecular docking of novel 1,8-naphthyridine derivatives and their cytotoxic activity against HepG2 cell lines" Med. Chem. Res 2014, 23, 76-86, Published online: May 17, 2013.*
Koopaei et al., "Synthesis and Analgesic Activity of Novel Hydrazide and Hydrazine Derivatives", Iran J Pharm Res., (2013) 12(4): 721-727.

* cited by examiner

*Primary Examiner* — David K O'Dell
(74) *Attorney, Agent, or Firm* — Richard C. Litman

(57) ABSTRACT

The naphthyridinyl hydrazine derivatives as potent peripheral analgesic agents are (E)-2-(substituted benzylidene)-1-(2,7-dialkyl-1,8-naphthyridinyl) hydrazines that provide effective peripheral analgesic activity, as demonstrated using the mouse writhing test. The new target compounds include at least one compound that demonstrates higher potency in providing analgesic relief in mice (Protection (%)=81.44) compared to the reference drug acetyl salicylic acid (Protection (%)=78.47). These results demonstrated that the target compound exerts acute analgesic action, suggesting that it may represent an alternative in the development of new therapeutic strategies. Preferably, the (E)-2-(substituted benzylidene)-1-(2,7-dialkyl naphthyridinyl) hydrazine has the formula:

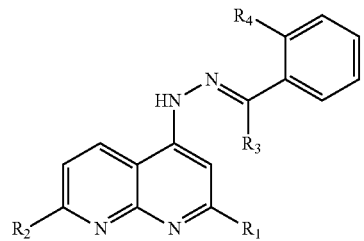

wherein $R_1$ and $R_2$ are alkyl, $R_3$ is hydrogen, and $R_4$ is $NO_2$.

1 Claim, 2 Drawing Sheets

NAPHTHYRIDINYL HYDRAZINE DERIVATIVES AS POTENT PERIPHERAL ANALGESIC AGENTS

BACKGROUND OF THE INVENTION

1. Field of the Invention

The present invention relates to naphthyridinyl hydrazine derivatives as potent peripheral analgesic agents, and particularly to (E)-2-(substituted benzylidene)-1-(2,7-dialkyl naphthyridinyl) hydrazines that display acute analgesic properties for therapeutic treatment.

2. Description of the Related Art

Heterocyclic compounds that include naphthyridine fused rings serve as important target molecules in synthetic and chemotherapeutic chemistry. In particular, naphthyridine is a key scaffold for a variety of biologically active compounds, which are widely applied as biological probes because they are analgesic and anti-inflammatory agents devoid of unwanted side effects. In fact, naphthyridine derivatives exhibit appreciable analgesic and anti-inflammatory properties, while frequently lacking the acute gastrolesivity and significant acute toxicity substituents present in many current analgesic treating agents, such as nonsteroidal anti-inflammatory drugs (NSAIDs).

Furthermore, naphthyridine derivatives have been shown to exhibit a wide range of beneficial pharmacological effects, including, without limitation, antileishmanial, antimicrobial, anticancer, antihypertensive, antiproliferative, antimalarial, immunomodulatory, and anti-inflammatory effects. Thus, identification of new naphthyridinyl hydrazine compounds that serve as potent peripheral analgesic agents may help provide a new generation of safe treating agents that provide efficacy and avoid causing problems frequently associated with many current therapeutic agents.

Thus, naphthyridinyl hydrazine derivatives as potent peripheral analgesic agents solving the aforementioned problems are desired.

SUMMARY OF THE INVENTION

The naphthyridinyl hydrazine derivatives as potent peripheral analgesic agents are novel (E)-2-(substituted benzylidene)-1-(2,7-dialkyl-1,8-naphthyridinyl) hydrazines that provide effective peripheral analgesic activity, as demonstrated using the mouse writhing test. The new target compounds include at least one compound that demonstrates higher potency in providing analgesic relief in mice (Protection (%)=81.44) compared to the reference drug acetyl salicylic acid (Protection (%)=78.47). These results demonstrated that the target compound exerts acute analgesic action, suggesting that it may represent an alternative in the development of new therapeutic strategies.

In a preferred embodiment, the (E)-2-(substituted benzylidene)-1-(2,7-dialkyl naphthyridinyl) hydrazine has the formula:

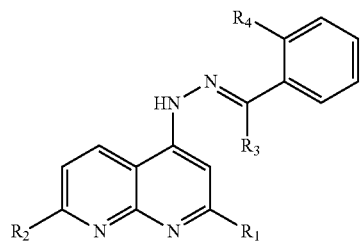

wherein $R_1$ and $R_2$ are alkyl, $R_3$ is hydrogen, and $R_4$ is $NO_2$.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The naphthyridinyl hydrazine derivatives as potent peripheral analgesic agents include an (E)-2-(nitrobenzylidene)-1-(2,7-dialkyl naphthyridinyl)hydrazine derivative bearing a Schiff base moiety at the 4-position, which was designed to obtain effective and promising peripheral analgesic activity. The target product appeared to be more potent, and displayed very interesting analgesic properties in mice (Protection (%)=81.44), more than the reference drug, acetylsalicylic acid (Protection (%)=78.47). This result demonstrated that the target compound exerts acute analgesic action, suggesting that it may represent an alternative in the development of future new therapeutic strategies.

In a preferred embodiment, the (E)-2-(substituted benzylidene)-1-(2,7-dialkyl naphthyridinyl)hydrazine has the following chemical structure:

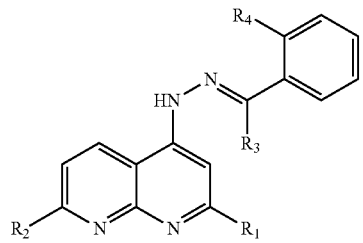

where $R_1$ and $R_2$ are alkyl, $R_3$ is hydrogen, and $R_4$ is $NO_2$.

Figure 1:
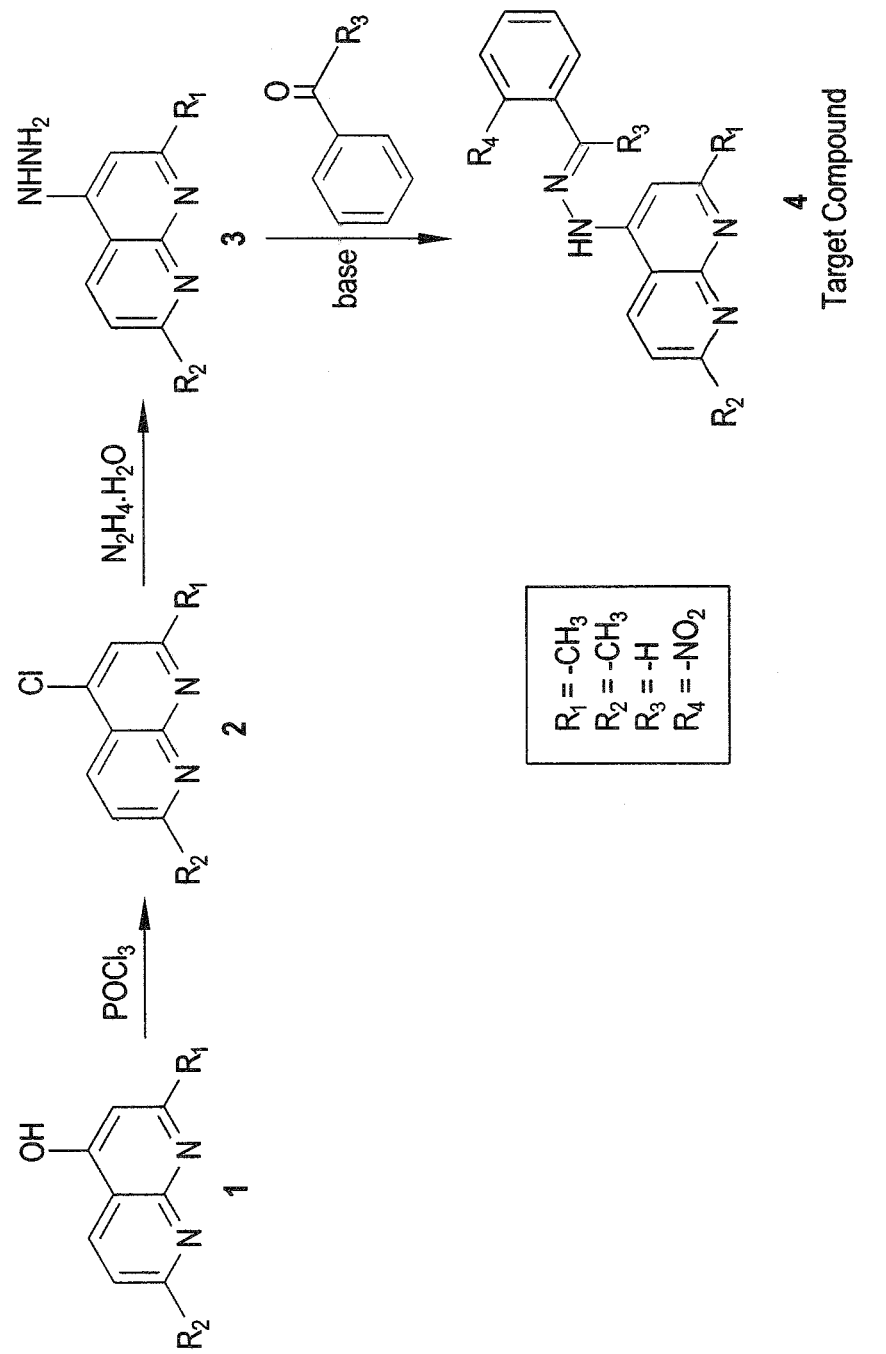
FIG. 1 is a reaction scheme for the synthesis of a naphthyridinyl hydrazine derivative (referred to herein as compound 9) according to the present invention.

A synthetic pathway leading to certain target compounds is set forth in FIG. 1. Generically, starting material 4-hydroxy-2,7-dialkyl-1,8-naphthyridine 1 is chlorinated with an excess of $POCl_3$, affording good yields of the corresponding 4-chloro-derivative 2, which is followed by condensation with hydrazine hydrate to give the desired 4-hydrazinyl-2, 7-dialkyl-1,8-naphthyridine (compound 3 in FIG. 1). Reaction of the hydrazine derivative 3 with substituted aromatic ketone produces the target compound 4, which can be confirmed by various physical and spectroscopic analysis. (It will be understood that in the reaction scheme shown in FIG. 1, the benzyl moiety of the ketone in the reaction proceeding from compound 3 to compound 4 may be substituted with a nitro (—$NO_2$) substituent at any one of the carbons in the ring, and that the position of $R_4$ shown in compound 4 of FIG. 1 is exemplary only, i.e., the nitro substituent may be attached to any one of the carbons of the benzylidene ring.)

The naphthyridinyl hydrazine derivatives as potent peripheral analgesic agents will be better understood with reference to the following examples. In order to explore the potential use of naphthyridinyl hydrazine derivatives as peripheral analgesic agents, the present inventors synthesized ten such compounds and tested the ten compounds versus a placebo control and acetylsalicylic acid as a standard analgesic agent by mouse writhing test. In the following examples, melting points were determined using the Electro-thermal IA 9100 melting point apparatus, the results of which are uncorrected. Elemental microanalysis was found within the agreeable limits of the calculated values. IR spectra (v, $cm^{-1}$) were run with a Schimadzu 435 IR Spectrophotometer using KBr pellets. $^1H$ and $^{13}C$ NMR spectra ((DMSO-$d_6$), δ, ppm) were obtained with a Varian Gemini 500 MHz Spectrophotometer using tetramethylsilane (TMS) as an internal standard. Mass Spectra were recorded on a Hewlett Packard 5988 Spectrometer. TLC-analysis was carried out on silica gel aluminum sheets, 60 $F_{254}$ for reaction progress.

EXAMPLE 1

General Synthesis Procedure

One of ten different active ketones or aldehydes (specified in the following examples) was added to a suspension of hydrazide derivative (10 mmol of compound 3, shown in FIG. 1) in dry ethanol (30 mL) in the presence of a catalytic amount of piperidine. The reaction mixture was refluxed for 5-8 hours while being monitored by TLC. The mixture was then left to cool to room temperature. The reaction mixture was concentrated under reduced pressure, and the resulting precipitate was filtered off, dried, and recrystallized from the proper solvent to produce products 1 to 10.

EXAMPLE 2

Synthesis of Test Compound 1

Test compound 1 was synthesized according to the procedure of Example 1 in which the aldehyde used was 4-morpholinobenzaldehyde. Characterization by the test procedures described above confirmed that test compound 1 has the formula:

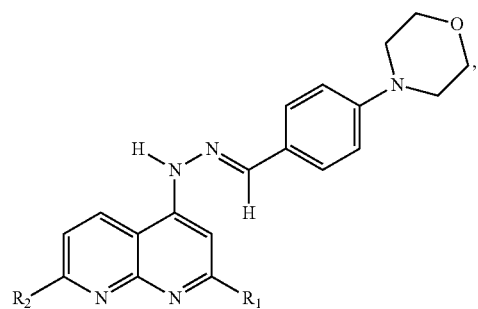

wherein $R_1$ and $R_2$ are methyl.

EXAMPLE 3

Synthesis of Test Compound 2

Test compound 2 was synthesized according to the procedure of Example 1 in which the aldehyde used was 4-(piperazin-1-yl)benzaldehyde. Characterization by the test procedures described above confirmed that test compound 2 has the formula:

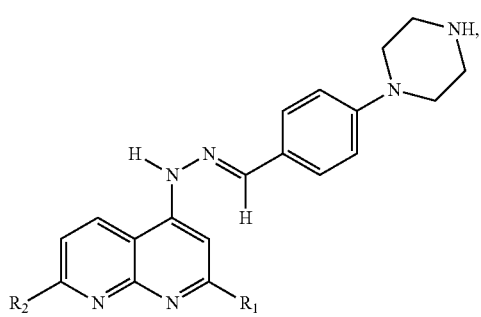

wherein $R_1$ and $R_2$ are methyl.

EXAMPLE 4

Synthesis of Test Compound 3

Test compound 3 was synthesized according to the procedure of Example 1 in which the aldehyde used was 4-(piperidin-1-yl)benzaldehyde. Characterization by the test procedures described above confirmed that test compound 3 has the formula:

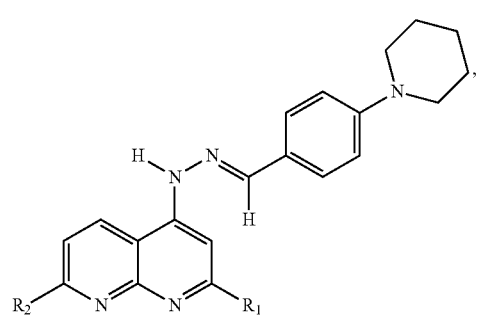

wherein $R_1$ and $R_2$ are methyl.

EXAMPLE 5

Synthesis of Test Compound 4

Test compound 4 was synthesized according to the procedure of Example 1 in which the aldehyde used was 4-(4-methylpiperazin-1-yl)benzaldehyde. Characterization by the test procedures described above confirmed that test compound 4 has the formula:

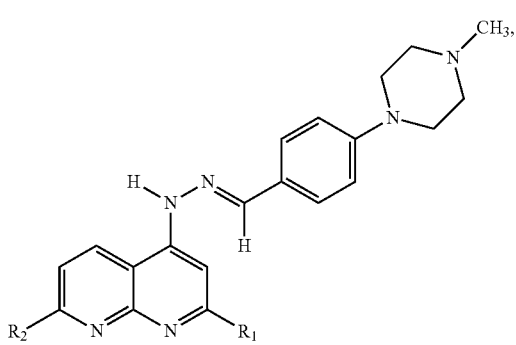

wherein $R_1$ and $R_2$ are methyl.

EXAMPLE 6

Synthesis of Test Compound 5

Test compound 5 was synthesized according to the procedure of Example 1 in which the ketone used was 1-(4-morpholino phenyl)ethanone. Characterization by the test procedures described above confirmed that test compound 5 has the formula:

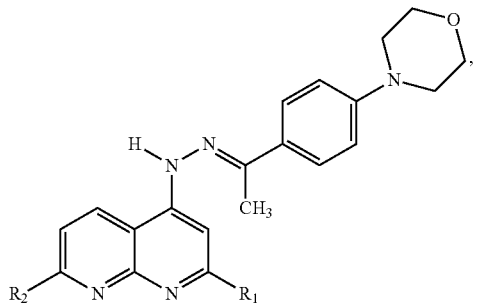

wherein $R_1$ and $R_2$ are methyl.

EXAMPLE 7

Synthesis of Test Compound 6

Test compound 6 was synthesized according to the procedure of Example 1 in which the ketone used was 1-(4-(piperazin-1-yl)phenyl)ethanone. Characterization by the test procedures described above confirmed that test compound 6 has the formula:

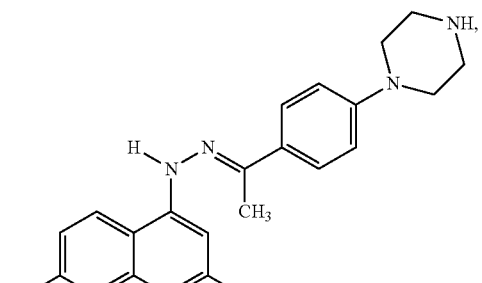

wherein $R_1$ and $R_2$ are methyl.

EXAMPLE 8

Synthesis of Test Compound 7

Test compound 7 was synthesized according to the procedure of Example 1 in which the ketone used was 1-(4-(piperidin-1-yl)phenyl)ethanone. Characterization by the test procedures described above confirmed that test compound 7 has the formula:

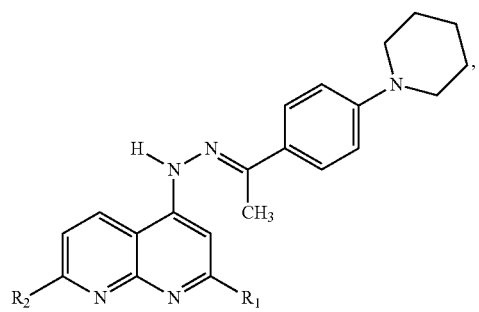

wherein $R_1$ and $R_2$ are methyl.

EXAMPLE 9

Synthesis of Test Compound 8

Test compound 8 was synthesized according to the procedure of Example 1 in which the ketone used was 1-(4-(4-methylpiperazin-1-yl)phenyl)ethanone. Characterization by the test procedures described above confirmed that test compound 8 has the formula:

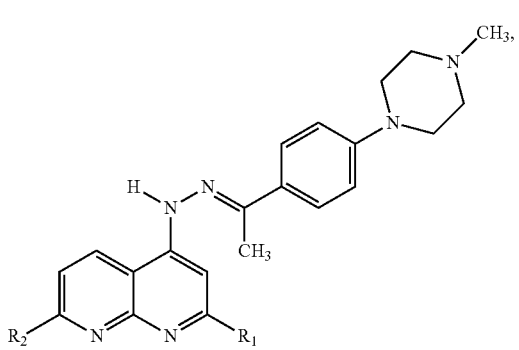

wherein $R_1$ and $R_2$ are methyl.

EXAMPLE 10

Synthesis of Test Compound 9

Test compound 9 was synthesized according to the procedure of Example 1 in which the aldehyde used was o-nitrobenzaldehyde. Characterization by the test procedures described above confirmed that test compound 9 has the formula:

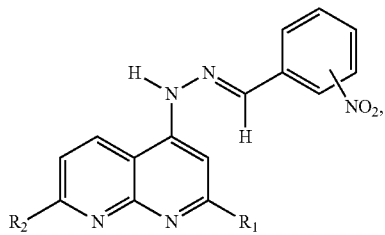

wherein $R_1$ and $R_2$ are methyl. In particular, compound 9 (also referred to herein as the target compound) was obtained by filtering the precipitate, following by washing with cold ethanol, drying, and recrystallization from solvent, resulting in 77% yield. MP 276-278° C.; IR (KBr, cm$^{-1}$) $v_{max}$: 3276 (NH), 1634 (C=N); $^1$H NMR (DMSO-d$_6$) δ: 2.61 (s, 6H, 2CH$_3$), 6.65-8.78 (m, 8H, Ar—H+12 ethane proton), 9.86 (s, 1H, NH, D$_2$O exchangeable); $^{13}$C NMR (DMSO-d$_6$) δ: 23.79, 110.35, 120.58, 121.15, 123.87, 125.96, 129.78, 131.54, 134.28, 136.01, 142.65, 149.12, 154.98, 157.43, 158.02, 160.10; MS: m/z 321 [M]$^+$. Calculated mass for C$_{17}$H$_{15}$N$_5$O$_2$ (321.33): C 63.54; H 4.71; N 21.79. Mass found: C63.37; H 4.55; N 21.63.

EXAMPLE 11

Synthesis of Test Compound 10

Test compound 10 was synthesized according to the procedure of Example 1 in which the aldehyde used was D-ribose. Characterization by the test procedures described above confirmed that test compound 10 has the formula:

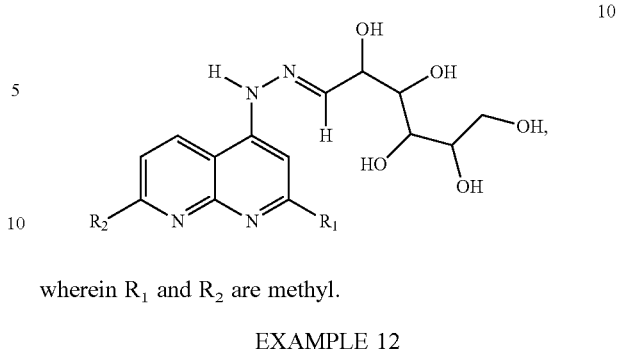

wherein $R_1$ and $R_2$ are methyl.

EXAMPLE 12

Testing for Analgesic Activity

The test compounds synthesized in Examples 2-11 were tested for analgesic activity as follows. Albino mice of both sexes (27-30 g body weight each) were used in the experiments. Mice used in this experiment were obtained from the Animal House Colony at the National Research Centre (NRC), Egypt. All animals were housed under standard conditions of natural 12-hour light and dark cycles with free access to food and water. Animals were allowed to adapt to the laboratory environment for one week before use in experimentation. All animal procedures were first approved by the Ethics Committee of the NRC, Egypt, and were performed in accordance with standard recommendations and guidelines for proper care and use of laboratory animals.

The peripheral analgesic activities of compounds 1 to 10 were determined in mice using the standard writhing test. Seventy-two mice were divided into 12 groups of 6 mice. Mice of the first (placebo control) and last (active control) groups were treated orally (p.o.) with the vehicle (5 mL/kg) or acetyl salicylic acid (150 mg/kg), respectively. Animals of the second to eleventh groups were orally given one of the selected compounds at doses of 20 mg/kg. Once 30 minutes passed after administration of medication, each mouse received an intraperitoneal injection of acetic acid (0.7% aqueous solution) in a dose of 10 mL/kg to induce writhing. The mice were then placed in transparent boxes, and the number of writhes per animal was counted for 20 minutes after acetic acid injection. The "protection %" was calculated using the following equation:

Protection (%)=[Control mean−Treated mean/Control mean]×100.

Figure 2:
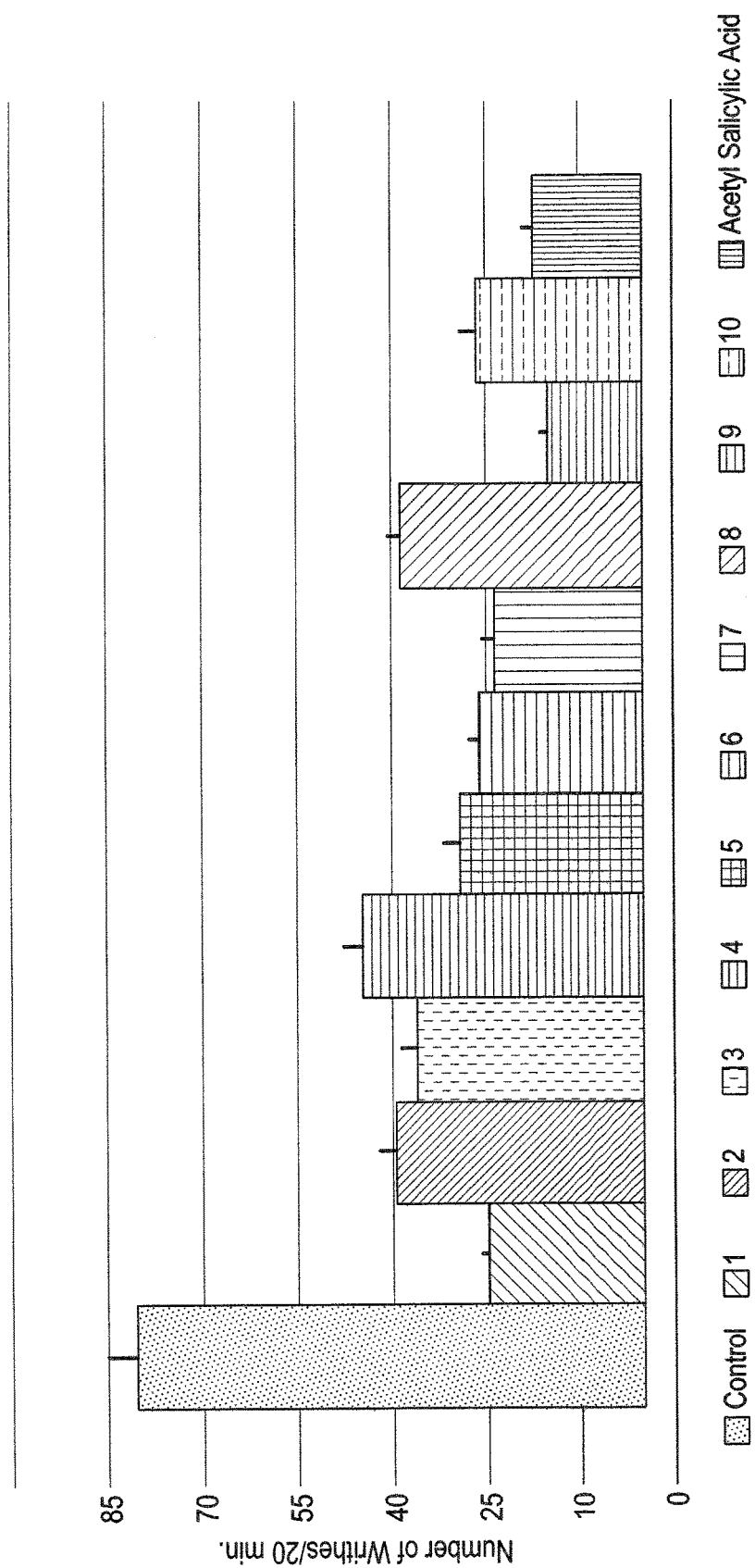
FIG. 2 is a bar chart demonstrating results from the mouse writhing test, comparing analgesic activity of 10 synthesized test compounds, showing relative number of writhes per 20 minutes, as compared to both a placebo control and acetylsalicylic acid.

The data are shown in Table 1 and the results are shown in FIG. 2.

TABLE 1

Peripheral analgesic activity of synthesized compounds

| Group | No. of writhes/20 min | Protection (%) |
|---|---|---|
| Control | 80.8 ± 4.47‡ | — |
| 1 | 24.8 ± 1.02* | 69.31 |
| 2 | 39.6 ± 3.14*‡ | 50.99 |
| 3 | 36.2 ± 2.58*‡ | 55.20 |
| 4 | 44.8 ± 2.85*‡ | 44.55 |
| 5 | 29.2 ± 2.50*‡ | 63.86 |
| 6 | 26.2 ± 1.32* | 67.57 |
| 7 | 23.6 ± 2.16* | 70.79 |
| 8 | 38.8 ± 1.77*‡ | 51.98 |
| 9 | 15.0 ± 1.14* | 81.44 |

TABLE 1-continued

Peripheral analgesic activity of synthesized compounds

| Group | No. of writhes/20 min | Protection (%) |
|---|---|---|
| 10 | 26.4 ± 2.46* | 67.33 |
| Acetylsalicylic acid | 17.4 ± 1.57* | 78.47 |

Values represent the mean ± S.E. of five mice for each group.
*$P < 0.05$: Statistically significant from control (Dunnett's test).
‡$P < 0.05$: Statistically significant from acetyl salicylic acid (Dunnett's test).
All drugs were dissolved in DMSO (20 mg/kg, orally), except acetylsalicylic acid was dissolved in DW, 150 mg/kg, orally.

The results clearly show that compound 9 produced greater analgesic activity than acetyl salicylic acid. Compounds 1, 6, 7, and 10 also produced analgesic activity close to that of acetylsalicylic acid. Indeed, all of the results from these four compounds were not statistically significantly different from the results for acetylsalicylic acid. At the same time, all ten samples tested (and the acetyl salicylic acid) resulted in degrees of analgesic activity that were statistically significantly different from the placebo control.

It is to be understood that the present invention is not limited to the embodiments described above, but encompasses any and all embodiments within the scope of the following claims.

We claim:

1. A naphthyridinyl hydrazine derivative for providing peripheral analgesic relief having the formula:

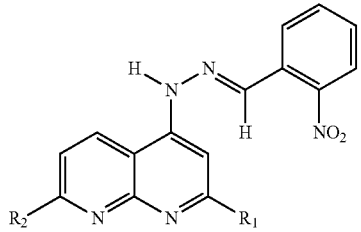

wherein $R_1$ and $R_2$ are methyl.

* * * * *